United States Patent
Kim et al.

(10) Patent No.: US 9,938,487 B2
(45) Date of Patent: Apr. 10, 2018

(54) METHOD FOR PREPARING FATTY ACID ALKYL ESTER USING FAT

(71) Applicant: SK CHEMICALS CO., LTD., Gyeonggi-do (KR)

(72) Inventors: Soo-Hyun Kim, Incheon (KR); Hyun Jun Cho, Gyeonggi-do (KR); Mi-Ran Lee, Incheon (KR)

(73) Assignee: SK CHEMICALS CO., LTD., Gyeonggi-do (KR)

( * ) Notice: Subject to any disclaimer, the term of this patent is extended or adjusted under 35 U.S.C. 154(b) by 0 days.

(21) Appl. No.: 14/905,470

(22) PCT Filed: Jul. 18, 2014

(86) PCT No.: PCT/KR2014/006562
§ 371 (c)(1),
(2) Date: Jan. 15, 2016

(87) PCT Pub. No.: WO2015/012538
PCT Pub. Date: Jan. 29, 2015

(65) Prior Publication Data
US 2016/0152908 A1  Jun. 2, 2016

(30) Foreign Application Priority Data
Jul. 22, 2013 (KR) .................. 10-2013-0086041

(51) Int. Cl.
*C11C 3/00* (2006.01)
*C10L 1/02* (2006.01)
(Continued)

(52) U.S. Cl.
CPC .............. *C11C 3/003* (2013.01); *C07C 67/03* (2013.01); *C10L 1/026* (2013.01); *C11C 1/04* (2013.01);
(Continued)

(58) Field of Classification Search
CPC . C11C 3/003; C11C 1/04; C07C 67/08; Y02E 50/13; C10L 2200/0476
See application file for complete search history.

(56) References Cited

U.S. PATENT DOCUMENTS 4,164,506 A   8/1979  Kawahara et al.
4,608,202 A   8/1986  Lepper et al.
(Continued)

FOREIGN PATENT DOCUMENTS

EP   0 127 104 A1   12/1984
EP   0 184 740 A2   6/1986
(Continued)

OTHER PUBLICATIONS

JP 2007009017, Univ Koyoto, 2007, Method for producing fatty acid alkyl ester, English translation 15 pages.*
(Continued)

*Primary Examiner* — Yate K Cutliff
(74) *Attorney, Agent, or Firm* — Collard & Roe, P.C.

(57) ABSTRACT

Disclosed is a method for preparing fatty acid alkyl ester for bio-diesel fuels by reacting a raw material containing fat with water to prepare fatty acid, and then reacting the prepared fatty acid with alcohol. The method for preparing fatty acid alkyl ester for bio-diesel fuels includes the steps of: preparing fatty acid and glycerin by an hydrolysis reaction of a raw material containing fat and water at the temperature of 200 to 280° C. and the pressure of 30 to 80 bar; carrying out a phase separation of the fatty acid and the glycerin; and carrying out an esterification reaction of the separated fatty acid and alcohol at the temperature of 200 to 350° C. and the pressure of atmospheric pressure to 35 bar.

1 Claim, 1 Drawing Sheet

(51) Int. Cl.
*C07C 67/03* (2006.01)
*C11C 1/04* (2006.01)

(52) U.S. Cl.
CPC . *C10L 2200/0476* (2013.01); *C10L 2270/026* (2013.01); *Y02E 50/13* (2013.01); *Y02P 30/20* (2015.11)

(56) References Cited

U.S. PATENT DOCUMENTS

| | | | |
|---|---|---|---|
| 4,652,406 | A | 3/1987 | Lepper et al. |
| 5,849,939 | A | 12/1998 | Mittelbach et al. |
| 6,855,838 | B2 | 2/2005 | Haas et al. |
| 7,126,019 | B2 * | 10/2006 | Bloom ............... C11C 1/04 554/206 |
| 7,256,301 | B2 | 8/2007 | Erguen et al. |
| 7,795,460 | B2 | 9/2010 | Elliott |
| 2007/0185341 | A1 | 8/2007 | Ergun et al. |
| 2010/0228042 | A1* | 9/2010 | Chun ............... B01J 14/00 554/162 |
| 2011/0144375 | A1 | 6/2011 | Chaturvedi et al. |

FOREIGN PATENT DOCUMENTS

| | | |
|---|---|---|
| EP | 0 708 813 B1 | 12/1996 |
| JP | 2004-263011 A | 9/2004 |
| JP | 2007-009017 A | 1/2007 |
| JP | 2008-031257 A | 2/2008 |
| JP | 05-090676 B2 | 12/2012 |
| KR | 2004-0087625 A | 10/2004 |
| KR | 2004-0101446 A | 12/2004 |
| WO | 03/087278 A1 | 10/2003 |

OTHER PUBLICATIONS

International Search Report of PCT/KR2014/006562, dated Nov. 25, 2014.

International Preliminary Report on Patentability and Written Opinion of the International Searching Authority of PCT/KR2014/006562, dated Jan. 26, 2016 with English translation.

Minami, Eiji et al., "Kinetics of hydrolysis and methyl esterification for biodiesel production in two-step supercritical methanol process", Fuel, Dec. 2006, vol. 85, issues 17-18, pp. 2479-2483.

Kim, Manhoe et al., "Performance of heterogeneous ZrO2 supported metaloxide catalysts for brown grease esterification and sulfur removal", Bioresource Technology 102 (2011) pp. 2380-2386.

Oil Seeds, Oil and Fats vol. II—Oils and Fats Processing by E. Bernardini, 2nd Ed., p. 434, (3 pages).

* cited by examiner

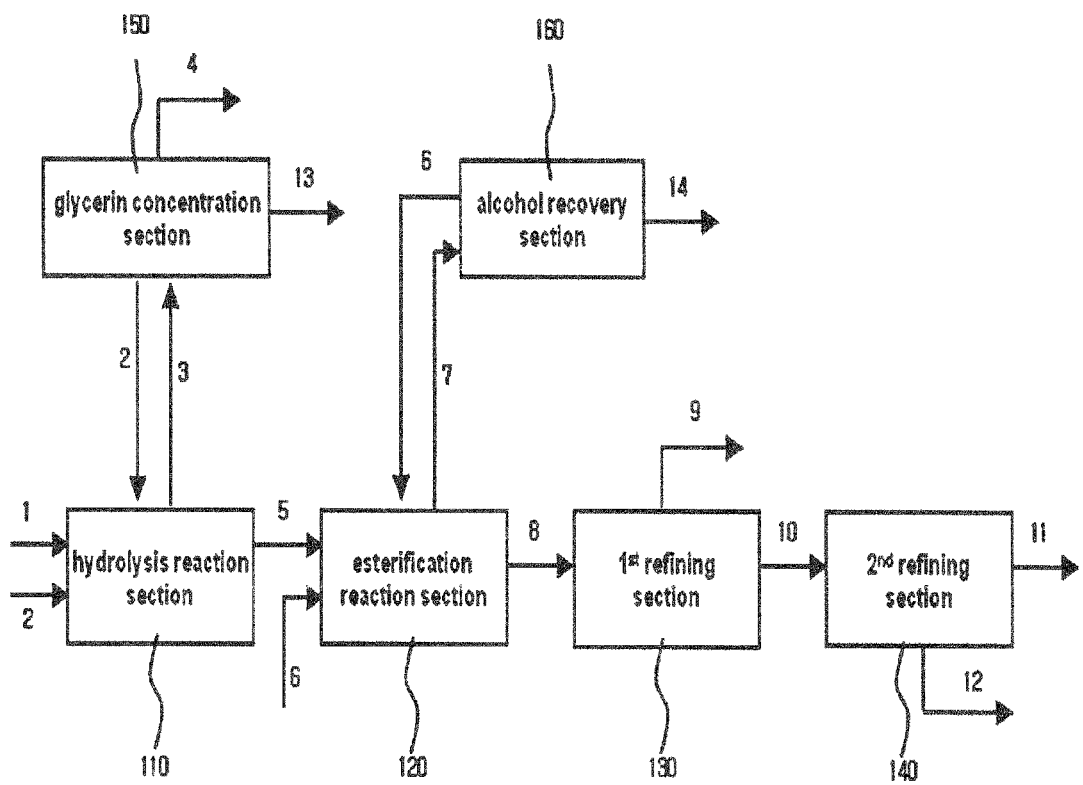

METHOD FOR PREPARING FATTY ACID ALKYL ESTER USING FAT

CROSS REFERENCE TO RELATED APPLICATIONS

This application is the National Stage of PCT/KR2014/006562 filed on Jul. 18, 2014, which claims priority under 35 U.S.C. §119 of Korean Application No. 10-2013-0086041 filed on Jul. 22, 2013, the disclosures of which are incorporated by reference. The international application under PCT article 21(2) was not published in English.

TECHNICAL FIELD

This invention relates to a method for preparing fatty acid alkyl ester using fat, and more particularly to a method for preparing fatty acid alkyl ester for bio-diesel fuels by reacting a raw material containing fat with water to prepare fatty acid, and then reacting the prepared fatty acid with alcohol.

BACKGROUND ART

Diesel, among the various fuels derived from crude mineral oils, has some advantages such as good fuel efficiency, low cost and low carbon dioxide generation. On the other hand, there is a problem that the combustion of diesel produces a large quantity of air pollution. In order to solve these problems, various researches have been actively conducted on the bio-diesel as an alternative fuel of diesel. The bio-diesel has similar physical property to the traditional diesel oil, remarkably reduces air pollution, and is naturally recycling energy source. Generally, the bio-diesel is produced by transesterification reaction of vegetable oil such as rapeseed oil, soybean oil, sunflower oil, palm oil, etc, animal fats, waste-cooking oil, and so on with alcohol in the presence of acid catalyst or alkali catalyst. As the raw material of the source of bio-diesel, oil from the vegetables such rapeseed, soybean, sunflower, coconut palm etc. has been commonly used. Recently, the production of bio-diesel is rapidly and world-widely increasing so that the cost of the raw material for preparing bio-diesel also increases, which causes problems of food shortage and farmland demolition. Thus, there has been a demand on a method for preparing bio-diesel using a non-edible raw material.

On the other hand, crude oils or sludge oils which are produced during an oil-expelling step and include relatively large amount of fatty acid, acidulated soap stock (acid oils) which are produced as a by-product during an oil-refining step, greases which are discharged from households or restaurants etc. contain a large amount of impurities as well as a large amount of free fatty acids. Thus they are classified to representative non-edible oils. In detail, examples of the non-edible oils include i) sludge oils and waste oils separated from the waste water which is generated from the processes of cleaning, sterilization, crushing and so on, during the vegetable or animal oil-expelling process (oil extraction process), ii) crude oils including a large amount of fatty acid inherently, for example, including more than 3 weight % of fatty acid, such as microalgae oils or oils obtained from the rancid vegetables or animals, iii) acidulated soap stock (Soap stock, Acid oil) which is reduced to the fatty acid by acidification or soap-splitting of fatty acid salt (soap) generated at the neutralization process for removing fatty acids during an oil-refining step, iv) used cooking oil (yellow grease, fryer grease) including large amount of fatty acid, which is collected after high-temperature deep-frying with large amount of butter and oils at households or restaurants, v) trap grease (brown grease or FOG (Fats, Oils, Grease)) including large amount of fatty acid, which is separated from water at a grease trap which is installed in a drainpipe of a house or a restaurant, and so on. In case where the above-mentioned non-edible oils are used as the raw material for preparing the bio-diesel, it is difficult to prepare fuels satisfying the quality standard. Also, pre-treatment or refining reaction step is inevitable for removing fatty acid or for converting fatty acid to the bio-diesel. Thus, the reaction time and the reaction steps increase and the total manufacturing cost for preparing bio-diesel increases. Accordingly, it has been generally known that the fats containing large amount of fatty acids are not suitable as the raw materials for preparing bio-diesel.

As described above, the vegetable or animal fats and oils of triglyceride form are generally used as the raw materials for preparing the bio-diesel. However, when these raw materials include free fatty acids, the reaction efficiency is deteriorated. Thus, in order to increase the reaction efficiency and to improve the quality of the prepared fatty alkyl ester, several methods are developed. For example, in European patent publication No. 127104A, European patent publication No. 184740A and U.S. Pat. No. 4,164,506, and so on, a two-step method is disclosed in which the free fatty acids in oils and fats is first esterified and then the transesterification of oils and fats are carried out. In the methods, the esterification reaction is carried out by heating the mixture of fatty acid and fatty acid triglyceride with methanol at about 65° C. in the presence of sulfuric acid or sulfonic acid catalyst. European patent publication No. 708813A discloses a method for increasing the yield of fatty acid alkyl ester from oils and fats. In the method, the free fatty acid is separated from glycerin phase which is prepared by a transesterification reaction, and then the separated free fatty acid is esterified. In this method, the free fatty acid is obtained by the neutralization of glycerin phase, and the obtained free fatty acid is reacted for 2 hours at about 85° C. in the presence of strong sulfuric acid catalyst, which reduces the amount of fatty acid from 50% to 12%.

In U.S. patent publication No. 2011/0144375A, Bioresource Technology 102 (2011, 2380-2386) and so on, the yield of fatty acid alkyl ester is improved by reacting a mixture of free fatty acids, oils and fats with alcohol in the presence of a ceramic catalyst and by carrying out an esterification reaction and a transesterification reaction simultaneously. In this method, large amount of the catalyst is necessary and water produced at the esterification reaction and glycerin produced at the transesterification reaction cannot be effectively discharged to the outside of the reaction system. Thus, the conversion ratio of fatty acid into fatty acid alkyl ester is low and also complicate processes including neutralization, filtration, cleaning, distillation should be carried out for using the prepared fatty acid alkyl ester as the bio-diesel. In U.S. Pat. Nos. 6,855,838 and 7,795,460 and so on, it is disclosed a method of firstly converting the mixture of free fatty acid, oils and fats into fatty acids and then esterifying the converted fatty acids. In this method, the mixture of free fatty acid, oils and fats is converted into the fatty acids by hydrolysis in the presence of sulfuric acid or a solid acid catalyst and the converted fatty acids is esterified in the presence of sulfuric acid or on exchange resins.

In addition, methods for improving esterification reaction efficiency of fatty acid are disclosed, which utilize a mechanical apparatus or supersonic waves for causing dynamic turbulence in a reactor (Korean patent publication No. 2004-0101446, International Publication No. WO 2003/087278). In this method, the esterification is carried out by reacting the fatty acid and/or fatty acid contained in oils and fats with alcohol at a high pressure and a high temperature in the presence of sulfuric acid or ion exchange resin catalyst. Further, Korean patent publication No. 2004-87625 discloses a method for removing free fatty acid from waste cooking oil, using solid acid catalyst. The above mentioned methods commonly use an acid catalyst, such as sulfuric acid etc. If such an acid catalyst is not completely removed after the reaction, the quality of bio-diesel is deteriorated. Therefore, complicate processes for neutralizing, filtering, washing and cleaning the acid catalyst should be carried out. In addition, the reactor should have a corrosion resistance against the acid catalyst, which increases the cost of the production facilities. Also, the life cycle of the solid acid catalyst is generally short, and the cost for recycling the catalyst is high. Furthermore, in the above mentioned conventional methods, since the esterification of fatty acid is carried out at low temperature, water produced during the reaction is not efficiently removed to the outside of the reaction system. Thus, the conversion ratio of fatty acid into fatty acid alkyl ester is low, and the physical properties of the obtained fatty acid alkyl ester are not suitable for bio-diesel.

DISCLOSURE

Technical Problem

Therefore, it is an object of the present invention to provide a method for economically and effectively preparing fatty acid alkyl ester suitable for bio-diesel fuel by using fat as a starting material.

It is other object of the present invention to provide a method for preparing fatty acid alkyl ester suitable for bio-diesel fuel by using a raw material containing fatty acid and fat such as vegetable or animal fats and oils, waste oils thereof, a by-product generated during a refining or treating process of vegetable or animal fats and oils, grease, and so on.

It is another object of the present invention to provide a method for preparing fatty acid alkyl ester by using fat, which does not needs a neutralization, a filtration, cleaning process and so on for removing a catalyst.

Technical Solution

In order to achieve these objects, the present invention provides a method for preparing fatty acid alkyl ester for bio-diesel fuels, comprising the steps of: preparing fatty acid and glycerin by an hydrolysis reaction of a raw material containing fat and water at the temperature of 200 to 280° C. and the pressure of 30 to 80 bar; carrying out a phase separation of the fatty acid and the glycerin; and carrying out an esterification reaction of the separated fatty acid and alcohol at the temperature of 200 to 350° C. and the pressure of atmospheric pressure to 35 bar.

Advantageous Effects

According to the method for preparing fatty acid alkyl ester of the present invention, fatty acid alkyl ester suitable for bio-diesel fuel can be economically and effectively prepared with a raw material containing fat component such as vegetable or animal fats and oils, waste oils thereof, a by-product generated during a refining or treating process of vegetable or animal fats and oils, grease, and so on. In addition, the method of the present invention does not require additional processes for removing a catalyst such as a neutralization, a filtration, a cleaning process and so on.

DESCRIPTION OF DRAWINGS

FIG. 1 is a drawing for showing the entire configuration of the apparatus for carrying out the method for preparing fatty acid alkyl ester of the present invention.

Mode for Invention

A more complete appreciation of the invention, and many of the attendant advantages thereof, will be better appreciated with reference to the following detailed description and the accompanying drawings.

To prepare fatty acid alkyl ester for bio-diesel fuel according to the present invention, firstly a raw material containing fat is reacted with water at high temperature and high pressure to produce fatty acid and glycerin (hydrolysis).

In the present invention, the "raw material containing fat" means a starting material (feedstock) which contains fat components (fat and/or fatty oil) which can be converted into fatty acid by a reaction with water. The "raw material containing fat" can be a pure fat such as a fat of a solid state at room temperature, oil or fatty oil of a liquid state at room temperature, or a mixture of the pure fat component and impurities such as fatty acid. In this specification, if necessary, the fat component such as fat and oil can be simply expressed as "fat". In the raw material, the amount of fat can be 5 to 100 weight %, preferably 10 to 99 weight %, more preferably 20 to 95 weight %, most preferably 30 to 85 weight %, and the amount of remaining impurities such as fatty acid can be 0 to 95 weight %, preferably 1 to 90 weight %, more preferably 5 to 80 weight %, most preferably 15 to 70 weight %. The fat component can be monoacylglycerol, diacylglycerol, triacylglycerol, and mixture thereof. For example, among the raw material, the amount of fatty acid can be 5 to 85 weight %, preferably 10 to 75 weight %, more preferably 15 to 70 weight %, and the amount of fat component (monoacylglycerol, diacylglycerol, triacylglycerol) can be 5 to 95 weight %, preferably 10 to 90 weight %, more preferably 15 to 85 weight %. When the amount of fat component and/or fatty acid is too small, the production of the fatty acid and/or fatty acid alkyl ester is decreased and thus total production yield is decreased. Further, in the fat component and the fatty acid component contained in the raw material, the amount of aliphatic hydrocarbon chain having 6 to 24 carbon atoms is 3 to 100 weight %, preferably 5 to 95 weight %, more preferably 15 to 90 weight %, most preferably 50 to 85 weight % with respect to total aliphatic hydrocarbon chain constituting the fat and fatty acid component, and the remaining aliphatic hydrocarbon chain has carbon atoms of less than 6 or more than 24. Examples of the "the raw material containing fat" include (i) a refined vegetable or animal fats and oils, (ii) vegetable crude fats and oils obtained from vegetables such as rapeseed, soybean, sunflower, palm, etc, (iii) animal crude fats and oils, (iv) a mixture of fats, oils and greases (FOGs) produced as a by-product in an oil refining process which heats vegetable or animal crude fats and oils with a high temperature steam, (v) a mixture of fatty acid and fat or fatty oil, (vi) crude oil, sludge oil or acidulated soap stock (Acid oil) including large amount of fatty acid which is generated in an oil-expelling or refining process, (vii) trap grease (Brown grease) separated from "sewage" or "vegetable or animal waste oil" which are discharged from houses or restaurants, and so on.

When iv) a mixture of fats, oils and grease (FOGs) of industrial or municipal waste, is used as the raw material, the present invention is preferable in environmental and economic aspects.

When the raw material containing fat is reacted with water, crude fatty acid and glycerin are produced by a hydrolysis reaction. The reaction temperature is 200 to 280° C., preferably 220 to 260° C., more preferably 240 to 260° C. and the reaction pressure is 30 to 80 bar, preferably 40 to 60 bar, more preferably 50 to 60 bar. When the reaction temperature is too low, the solubility of water in fat become lowered to decrease the reaction rate, the concentration of unreacted-fat increases due to a reaction equilibrium, and thereby the conversion ratio from fat to fatty acid decreases. When the reaction temperature is too high, organic materials can be thermally decomposed. Also, when the reaction pressure is too low, it is difficult for water among the reactant to be existed in a liquid-state so that the conversion ratio decreases. When the reaction pressure is too high, the reaction equipment should be prepared to endure the high pressure, and thereby the equipment cost increases. After producing crude fatty acid and glycerin with hydrolysis reaction in the manner as described above, a phase separation is carried out to separate fatty acid from the water and glycerin.

Next, the esterification reaction is carried out by reacting the separated fatty acid with alcohol to prepare fatty acid alkyl ester for bio-diesel fuel. As the alcohol for the esterification reaction, monovalent alcohols having 1 to 10 carbon atoms, preferably monovalent alcohols having 1 to 4 of carbon atom such as methanol, ethanol, propanol, or so on, and more preferably methanol, can be used. The temperature for the esterification reaction is 200 to 350° C., preferably 230 to 320° C., more preferably 250 to 300° C., and the pressure for the esterification reaction is atmospheric pressure to 35 bar, preferably 1 to 20 bar, more preferably 3 to 10 bar. When the esterification temperature is too low so that water in the reactants cannot be efficiently removed, unreacted fatty acid component remains at a reaction equilibrium state, which increases acid number (mg KOH/g) of fatty acid alkyl ester and thus the quality criteria for the bio-diesel cannot be satisfied. When the esterification temperature is too high, the organic materials can be thermally decomposed or carbonized. When the esterification pressure is too low, solubility of alcohol in gas-phase with respect to the reactant is low so that the reaction rate is decreased. When the esterification pressure is too high, the reaction equipment should be prepared to endure the high pressure, and thereby the equipment cost increases. Also, the water in the reactant cannot be effectively removed, and thereby unreacted fatty acid component remains at a reaction equilibrium state, which increases acid number (mg KOH/g) of fatty acid alkyl ester and thus the quality criteria for the bio-diesel cannot be satisfied. Once the esterification is completed in the manner as described above, a low-boiling impurity, a high-boiling impurity and fatty acid alkyl ester produced at the esterification reaction can be separated by distillations.

Next, the method for preparing fatty acid alkyl ester according to the present invention will be described with reference to FIG. 1. FIG. 1 shows the entire configuration of the apparatus which can be used for the method for preparing fatty acid alkyl ester according to an embodiment of the present invention. As shown in FIG. 1, the raw material containing fat 1 (hereinafter, if necessary, simply "raw material") and water 2 are introduced into a hydrolysis reaction section 110 and then hydrolysis reaction is carried out at high temperature and high pressure. Fatty acid 5 produced from the hydrolysis reaction and alcohol 6 are introduced to an esterification reaction section 120 and then the esterification reaction is carried out. The crude fatty acid alkyl ester 8 produced from the esterification reaction is transferred to a first refining section 130, and low-boiling impurities 9 can be discharged and removed through the top of the distillation column of the first refining section 130 by distillation. The first refined fatty acid alkyl ester 10 is transferred to a second refining section 140, and distilled to leave residual impurities 12 in the second refining section 140 and the distilled and purified fatty acid alkyl ester 11 is discharged through the top of the distillation column of the second refining section 140. The first refining section 130 operates at which the lower part of the distillation column of the first refining section 130 is under the vacuum condition of 0.1 to 150 torr and temperature of 150 to 250° C. so that the low-boiling impurities can be distilled off. The second refining section 140 operates at which the lower part of the distillation column of the second refining section 140 is under the vacuum condition of 0.1 to 150 torr and temperature of 200 to 300° C. so that the fatty acid alkyl ester having 6 to 24 carbon atoms in aliphatic part can be distilled.

Further, the hydrolysis reaction section 110 is provided with a glycerin concentration section 150 so that the glycerin produced at the hydrolysis reaction section 110 and excess unreacted water (water/glycerin 3, hereinafter, simply "sweet water") are transferred to the glycerin concentration section 150. The sweet water is concentrated in the glycerin concentration section 150 and then crude glycerin 4 is collected. In this case, some of the distilled water 2 is recycled to the hydrolysis reaction section 110 and the other part of the distilled water 13 is transferred to a waste water disposal plant. In addition, the esterification reaction section 120 is provided with a alcohol recovery section 160 so that the water produced at the esterification reaction section 120 and excess unreacted alcohol (alcohol/water 7) are transferred to the alcohol recovery section 160. In the alcohol recovery section 160, the alcohol 6 is distilled and recycled to the esterification reaction section 120 and the water 14 is transferred to the waste water disposal plant.

Hereinafter, the preferable examples are provided for better understanding of the present invention. However, the present invention is not limited to the following examples.

[Example 1] Preparation of Fatty Acid Alkyl Ester

A. Preparation of Fatty Acid

A hydrolysis reactor was maintained to the temperature of 250° C. and the pressure of 60 bar. To the upper part of the hydrolysis reactor was introduced palm acid oil containing 30 weight % of free fatty acid by 10 g/min of a flow rate and simultaneously to the lower part of the hydrolysis reactor was introduced water by 7 g/min of a flow rate, and the hydrolysis was carried out (retention time of the hydrolysis reaction: about 2 hours) to prepare crude fatty acid. The reaction product was obtained from the top part of the hydrolysis reactor and the obtained product was phase-separated so that the water/glycerin and the fatty acid were separated. Degree of splitting of the obtained fatty acid was 98.2. Herein, the degree of splitting is (acid value)/(saponification value) and is a conversion index of Hydrolysis process. The acid value represents the number of milligrams of potassium hydroxide required to neutralize 1 g of the free fatty acid and the saponification value represents the number of milligrams of potassium hydroxide required to saponify 1 g of fat or fatty acid. Accordingly, the degree of splitting represents the conversion degree of fat into fatty acid.

B. Preparation of Fatty Acid Methyl Ester

To a batch type reactor is injected 1 kg of fatty acid obtained at the Step A. The temperature and pressure of the batch type reactor were controlled to 300° C. and 7.5 bar. Then the esterification reaction was carried out for 3 hours while 430 g of methanol was continuously injected to the reactor to prepare fatty acid methyl ester. A conversion ratio of the obtained fatty acid methyl ester was 99.8%, and the final acid value was 0.25 mg/KOH/g.

[Example 2] Preparation of Fatty Acid Alkyl Ester

A. Preparation of Fatty Acid

A fatty acid was prepared in the same manner as the Step A of Example 1 except for using crude palm oil containing 14 weight % of free fatty acid instead of palm acid oil containing 30 weight % of free fatty acid. The degree of splitting (Acid Value/Saponification Value) of the obtained fatty acid was 98.5.

B. Preparation of Fatty Acid Methyl Ester

A fatty acid methyl ester was prepared in the same manner as the Step B of Example 1 except for controlling the pressure of the reactor being 5 bar. The conversion ratio and the final acid value of the obtained fatty acid methyl ester were 99.8% and 0.28 mg/KOH/g.

[Example 3] Preparation of Fatty Acid Alkyl Ester

A. Preparation of Fatty Acid

A fatty acid was prepared in the same manner as the Step A of Example 1 except for using brown grease containing 65 weight % of free fatty acid instead of palm acid oil containing 30 weight % of free fatty acid. The degree of splitting (Acid Value/Saponification Value) of the obtained fatty acid was 97.5.

B. Preparation of Fatty Add Methyl Ester

A fatty acid methyl ester was prepared in the same manner as the Step B of Example 1 except for controlling the pressure of the reactor being 5 bar. The conversion ratio and the final acid value of the obtained fatty acid methyl ester were 99.9% and 0.21 mg/KOH/g.

[Example 4] Preparation of Fatty Acid Alkyl Ester

A. Preparation of Fatty Acid

A fatty acid was prepared in the same manner as the Step A of Example 1 except for using acidulated soap sock (soybean based acid oil, Borra) containing 64 weight % of free fatty acid instead of palm acid oil containing 30 weight % of free fatty acid. The degree of splitting (Acid Value/Saponification Value) of the obtained fatty acid was 97.

B. Preparation of Fatty Acid Methyl Ester

A fatty acid methyl ester was prepared in the same manner as the Step B of Example 1 except for controlling the pressure of the reactor being 5 bar. The conversion ratio and the final acid value of the obtained fatty acid methyl ester were 99.8% and 0.34 mg/KOH/g.

[Example 5] Preparation of Fatty Acid Alkyl Ester

A. Preparation of Fatty Acid

A fatty acid was prepared in the same manner as the Step A of Example 1 except for using used cooking oil containing 5 weight % of free fatty acid instead of palm acid oil containing 30 weight % of free fatty acid. The degree of splitting (Acid Value/Saponification Value) of the obtained fatty acid was 97.3.

B. Preparation of Fatty Acid Methyl Ester

A fatty acid methyl ester was prepared in the same manner as the Step B of Example 1 except for controlling the temperature of the reactor being 250° C. The conversion ratio and the final acid value of the obtained fatty acid methyl ester were 99.8% and 0.3 mg/KOH/g.

[Example 6] Preparation of Fatty Acid Alkyl Ester

A. Preparation of Fatty Acid

A fatty acid was prepared in the same manner as the Step A of Example 5. The degree of splitting (Acid Value/Saponification Value) of the obtained fatty acid was 97.3.

B. Preparation of Fatty Acid Methyl Ester

A fatty acid methyl ester was prepared in the same manner as the Step B of Example 1 except for controlling the temperature of the reactor being 270° C. The conversion ratio and the final acid value of the obtained fatty acid methyl ester were 99.9% and 0.22 mg/KOH/g.

[Example 7] Preparation of Fatty Acid Alkyl Ester

A. Preparation of Fatty Acid

A batch type reactor was controlled to temperature of 260° C. and pressure of 47 bar. 500 g of palm acid oil containing 82 weight % of free fatty acid and 800 g of water were introduced to the reactor and then the hydrolysis reaction was carried out 2 hours to prepare crude fatty acid. The reaction product was layer-separated at the lower part of the reactor to separate water and glycerin and fatty acid, The degree of splitting of the obtained fatty acid was 94.5.

B. Preparation of Fatty Acid Methyl Ester

A fatty acid methyl ester was prepared in the same manner as the Step B of Example 1 except for controlling the temperature of the reactor being 290° C. and the pressure of the reactor being 20 bar. The conversion ratio and the final acid value of the obtained fatty acid methyl ester were 99.7% and 0.43 mg/KOH/g.

[Example 8] Preparation of Fatty Acid Alkyl Ester

A. Preparation of Fatty Acid

A crude fatty acid was prepared in the same manner as the Step A of Example 7 except for controlling the temperature of the reactor being 270° C. and the pressure of the reactor being 55 bar. The degree of splitting (Acid Value/Saponification Value) of the obtained fatty acid was 95.7.

B. Preparation of Fatty Acid Methyl Ester

A fatty acid methyl ester was prepared in the same manner as the Step B of Example 1 except for controlling the temperature of the reactor being 290° C. and the pressure of the reactor being 10 bar. The conversion ratio and the final acid value of the obtained fatty acid methyl ester were 99.8% and 0.38 mg/KOH/g.

[Example 9] Preparation of Fatty Acid Alkyl Ester

A. Preparation of Fatty Acid

A crude fatty acid was prepared in the same manner as the Step A of Example 7 except for using palm acid oil containing 58 weight % of free fatty acid instead of palm acid oil containing 82 weight % of free fatty acid, and controlling the temperature of the reactor being 280° C. and the pressure of the reactor being 64 bar. The degree of splitting (Acid Value/Saponification Value) of the obtained fatty acid was 94.4.

B. Preparation of Fatty Acid Methyl Ester

A fatty acid methyl ester was prepared in the same manner as the Step B of Example 1 except for controlling the temperature of the reactor being 290° C. and the pressure of the reactor being 7.5 bar. The conversion ratio and the final acid value of the obtained fatty acid methyl ester were 99.9% and 0.2 mg/KOH/g.

INDUSTRIAL APPLICABILITY

As described above, in the method for preparing fatty acid alkyl ester according to the present invention, unlikely to the conventional art, "the raw material containing fat" is used as the starting material, and the amount of fatty acid is increased by carrying out the hydrolysis reaction of fat and water at high temperature and high pressure and thereafter the esterification reaction of fatty acid with alcohol is carried out to produce fatty acid alkyl ester for bio-diesel fuel with high quality. Further since in the present invention, the hydrolysis reaction and the esterification reaction are carried out without catalyst, the fatty acid alkyl ester with high purity and high conversion ratio can be obtained only by simple distillation process without a neutralization, a filtration, cleaning process and so on for removing the catalyst.

Also, according to the present invention, even in case of using crude oils and fats, mixture of fat, oil, grease and so on which contain fatty acid of various concentration as the raw material, the fatty acid alkyl ester with high conversion ratio can be prepared.

The invention claimed is:

1. A method for preparing fatty acid alkyl ester for bio-diesel fuels, comprising the steps of:
   preparing fatty acid and glycerin by an hydrolysis reaction of a raw material containing fat and water at a temperature of 240 to 260° C. and a pressure of 50 to 60 bar;
   carrying out a phase separation to separate the fatty acid from the water and the glycerin; and
   carrying out an esterification reaction of the separated fatty acid and alcohol of gas phase at a temperature of 250 to 300° C. and a pressure of 3 to 10 bar so that water is removed during the esterification reaction and a fatty acid alkyl ester is obtained,
   wherein an acid value of the fatty acid alkyl ester is equal to or less than 0.43 mg/KOH/g and the raw material containing fat comprises 5 to 85 weight % of fatty acid.

* * * * *